United States Patent [19]

Masuzawa

[11] Patent Number: 4,841,585
[45] Date of Patent: Jun. 27, 1989

[54] SWINGABLE AND SLIDABLE BED APPARATUS

[75] Inventor: Yukikazu Masuzawa, Tochigi, Japan

[73] Assignee: Kabushiki Kaisha Toshiba, Kawasaki, Japan

[21] Appl. No.: 165,903

[22] Filed: Mar. 9, 1988

[30] Foreign Application Priority Data

Mar. 12, 1987 [JP] Japan .................................. 62-55344

[51] Int. Cl.⁴ .......................... A61G 7/00; A61B 6/04
[52] U.S. Cl. ........................................... 5/62; 378/209
[58] Field of Search .......................... 5/62, 63; 108/5; 269/323; 297/329; 378/179, 209

[56] References Cited

U.S. PATENT DOCUMENTS 2,534,623 12/1950 Pitts et al. ....................... 378/209 X
3,525,308  8/1970 Koopmans ....................... 269/323 X
3,532,862 10/1970 Craig et al. ........................... 269/323
4,579,323  4/1986 Brendl et al.
4,618,133 10/1986 Siczek ............................. 378/209 X

FOREIGN PATENT DOCUMENTS 1949763  4/1971 Fed. Rep. of Germany ...... 378/179
38-8704  5/1963 Japan .

OTHER PUBLICATIONS

Machine Design "Tilting of a Bed for an X-Ray Diagnostic Apparatus"; Y. Masuzawa; Dec. 1986 Edition issued by Nikkan Kogyo, pp. 66 to 71.

*Primary Examiner*—Alexander Grosz
*Assistant Examiner*—Michael F. Trettel
*Attorney, Agent, or Firm*—Oblon, Fisher, Spivak, McClelland & Maier

[57] ABSTRACT

An axis of rotation of a bed can be shifted in a direction in which it becomes remote from a floor when the bed is slid parallel to a patient-mounted plane while being swung, in a case where the swing angle is relatively small. The amount of elevation of the bed can be made larger than in a case where the axis of rotation is not shifted. The amount of slide of the bed can be thus made smaller than in the case wherein the axis of rotation is not shifted, in order to obtain a predetermined amount of elevation of the bed. As the result, the horizontal component of slide can be made smaller to thereby making smaller the space in which the bed can be swung and slid.

10 Claims, 6 Drawing Sheets

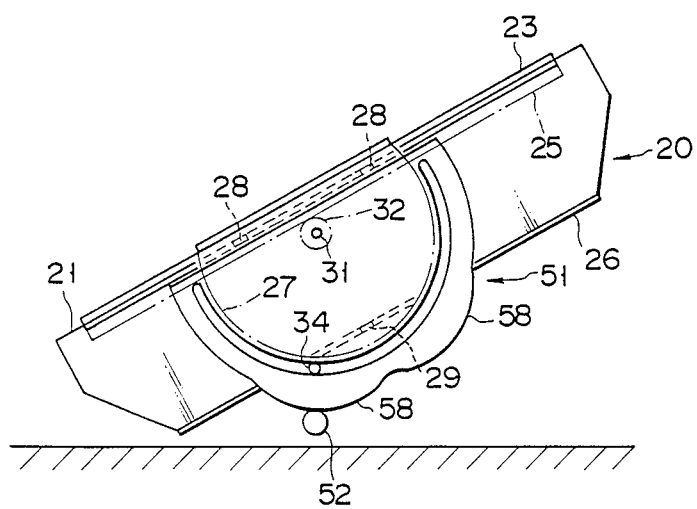
F I G. 8
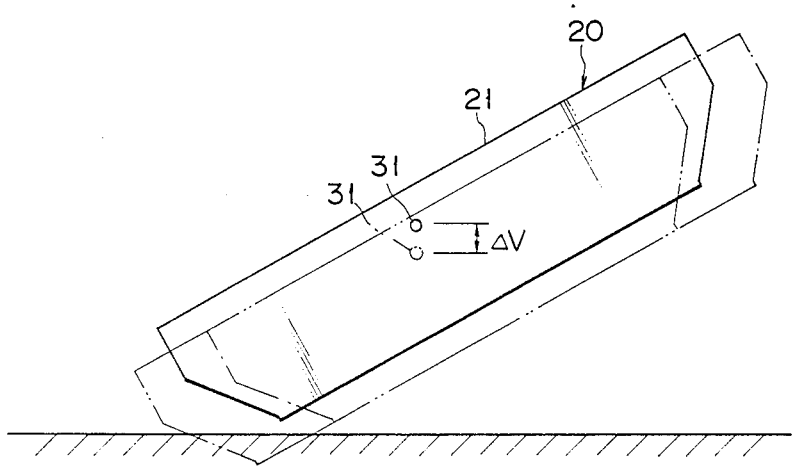
F I G. 9

SWINGABLE AND SLIDABLE BED APPARATUS

BACKGROUND OF THE INVENTION

The present invention relates to a swingable and slidable bed apparatus for use with the X-ray diagnostic device and the like.

When the alimentary canal and its related organs are to be diagnosed, an image forming agent having an X-ray absorption rate higher than that of the human body is used to take X-ray photographs of shapes of these organs. It is needed in this case that the image forming agent flows in the organs. The bed for use with the X-ray diagnostic device is therefore designed so that the patient horizontally lying on it can be shifted in posture to his standing normal or to his being fallen his head down. Bed 1 is therefore swung round the axis of rotation of support 2, as shown in FIG. 1.

The height of this type bed is preferably made so relatively low as to allow the patient to mount on it with easiness. When it is made low like this, it is also advantageous for the doctor to diagnose the patient lying on it, but it happens that floor 4 interferes with one end of it when it is swung. As shown in FIG. 2, therefore, it is slid, while being swung, parallel to that plane 5 of it on which the patient is lying, to prevent floor 4 from interfering with one end of it.

Guide rail 6 having rack 7 is attached to bed 1 along the upper rim thereof. Another guide rail 8 is attached to bed 1 along the lower rim thereof. Semi-circular gear 9 is rotatably supported by support 2. Cam followers 10 and 11 attached to semicircular gear 9 slide on guide rails 6 and 8. Pinion 13 is engaged with semicircular gear 9 and another pinion 12 is engaged with rack 7. Pinions 12 and 13 are respectively rotated at constant speed.

When pinions 12 and 13 are synchronously rotated, therefore, semicircular gear 9 is rotated while rack 7 is moved. As the result, bed 1 is slid parallel to plane 4 while being swung, as shown in FIG. 2. Because pinions 12 and 13 are respectively rotated at constant speed, the bed is swung while slid at constant speed (constant speed system). The bed is usually swung in a range of $-90°$ - $+90°$.

It is assumed in FIG. 2 that the amount of slide of the bed be denoted by S, the amount of maximum slide of the bed by Smax, the angle of swing (or inclined angle) of the bed by $\theta$, and the amount of elevation (or vertical component of slide amount) of the bed by V.

The relation among slide amount S, elevation amount V and swing angle $\theta$ is as follows.

$$S = (\theta/90°) \cdot Smax \qquad (1)$$

$$V = S \cdot \sin \theta \qquad (2)$$

When equation (1) is substituted by equation (2),
$$V = (\theta/90°) \cdot Smax \cdot \sin \theta \qquad (3)$$

The following can be understood from equations (1) and (3).

Slide amount S is proportional to swing angle $\theta$. As swing angle $\theta$ is increased, slide amount S is also increased in proportion to swing angle $\theta$.

Elevation amount V is not proportional to swing angle $\theta$. When swing angle $\theta$ is relatively small, elevation amount V is extremely small. When swing angle $\theta$ is relatively large, elevation amount V is relatively large. Namely, elevation amount V is increased as swing angle $\theta$ becomes larger and larger.

Further, the relation between the slide and the elevation amount can be understood from equation (2) as follows. When the swing angle is relatively small, the slide amount is extremely small in relation to the elevation amount. As shown in FIG. 3, for example, the slide amount is several times the elevation amount when swing angle $\theta$ equals to 30°. When the swing angle is relatively large, the slide amount becomes substantially equal to the elevation amount. As shown in FIG. 4, for example, the slide and the elevation amount are substantially equal when swing angle $\theta$ equals to 80°. When the slide amount is increased in a case where the swing angle is relatively large, therefore, the elevation amount is increased in corresponding with the amount of slide increased, but when the swing angle is relatively small, the elevation amount is increased a little even if the slide amount is increased.

When the swing angle is relatively small, therefore, the condition under which one end of the bed interferes with the floor can be improved better. The sliding speed of the bed is made higher with respect to the swinging speed of the bed in this case. When the swing angle is relatively small, the slide amount is thus increased rapidly to keep the elevation amount relatively large. When the sliding speed of the bed is made high, however, the slide amount becomes extremely large in a case where the swing angle is relatively large. Therefore, rack 7 of bed 1 comes out of pinion 12.

When the swing angle is relatively small, therefore, the sliding speed of the bed is made higher in relation to the swinging speed of the bed, while when the swing angle is relatively large, the sliding speed is made lower in relation to the swinging speed of the bed (speed change system), as shown in FIG. 5. The sliding speed is therefore changed two times relative to the swing angle. When the swing angle is relatively small, the slide amount is rapidly increased to keep the elevation amount relatively large, while when the swing angle is relatively large, the slide amount is not made extremely large. Maximum slide amount Smax is made equal to the maximum slide amount in the constant speed system (a driver means for this constant speed system is disclosed in an article "Swinging and Sliding of the Bed for Use with the X-ray Diagnostic Device" written by the inventor of the present invention for a magazine "Machine Designs" (Pages 66-71, December Edition, 1986) published by Nikkan Kogyo Shinbun).

However, this speed change system has such a drawback that horizontal component H of slide amount S becomes extremely large when swing angle $\theta$ is relatively small. Namely, the relation between this horizontal component H and slide amount S can be expressed as follows.

$$H = S \cdot \cos \theta \qquad (4)$$

When equation (1) is substituted by equation (4),
$$H = (\theta/90°) \cdot Smax \cdot \cos \theta \qquad (5)$$

When the value of Smax is set large in a case where the swing angle is relatively small, therefore, horizontal component H is rapidly increased.

Namely, when the slide amount is increased in a case where the swing angle is relatively small, elevation amount V is hardly increased but horizontal component H is rapidly increased, as apparent from equations (2) and (4). As the sliding speed is made higher and higher, therefore, the increasing ratio of horizontal component H becomes larger and larger.

When horizontal component H is made large like this in the case where the swing angle is relatively small, the traveling distance of the bed becomes long in the horizontal direction. As the result, the space in which the bed can be swung and slide becomes large.

SUMMARY OF THE INVENTION

The object of the present invention is to provide a swingable and slidable bed apparatus capable of making the moving amount of the bed small in the horizontal direction while keeping the elevation amount of the bed relatively large when the swing angle of the bed is relatively small, so that the space in which the bed can be swung and slid can be made smaller.

According to the present invention, there is provided a swingable and slidable bed apparatus supported on the floor and comprising: a bed having that plane on which a patient is mounted, and also having both ends and an axis of rotation round which the bed can be swung; a means for swinging the bed round the axis of rotation; a means for sliding the bed parallel to the patient-mounted plane while the bed is being swung; and a means for shifting the axis of rotation in a direction in which it becomes remote from the floor when the bed is slid parallel to the patient-mounted plane while being swung.

According to the present invention, the axis of rotation can be shifted in the direction in which it becomes remote from the floor when the bed is slid parallel to the patient-mounted plane while being swung. The amount of elevation of the bed can be made larger than in a case where the axis of rotation is not shifted. The amount of slide of the bed can be thus made smaller than in the case where the axis of rotation is not shifted, in order to obtain a predetermined amount of elevation of the bed. As the result, the horizontal component of slide can be made smaller to thereby making smaller the space in which the bed can be swung and slid.

BRIEF DESCRIPTION OF THE DRAWINGS

FIG. 8 is a front view showing the bed apparatus in FIG. 6 in which its bed is swung, slid and shifted;

FIG. 9 is a diagram showing the bed in FIG. 6 swung, slid and shifted;

DETAILED DESCRIPTION OF THE PREFERRED EMBODIMENTS

Figure 6:
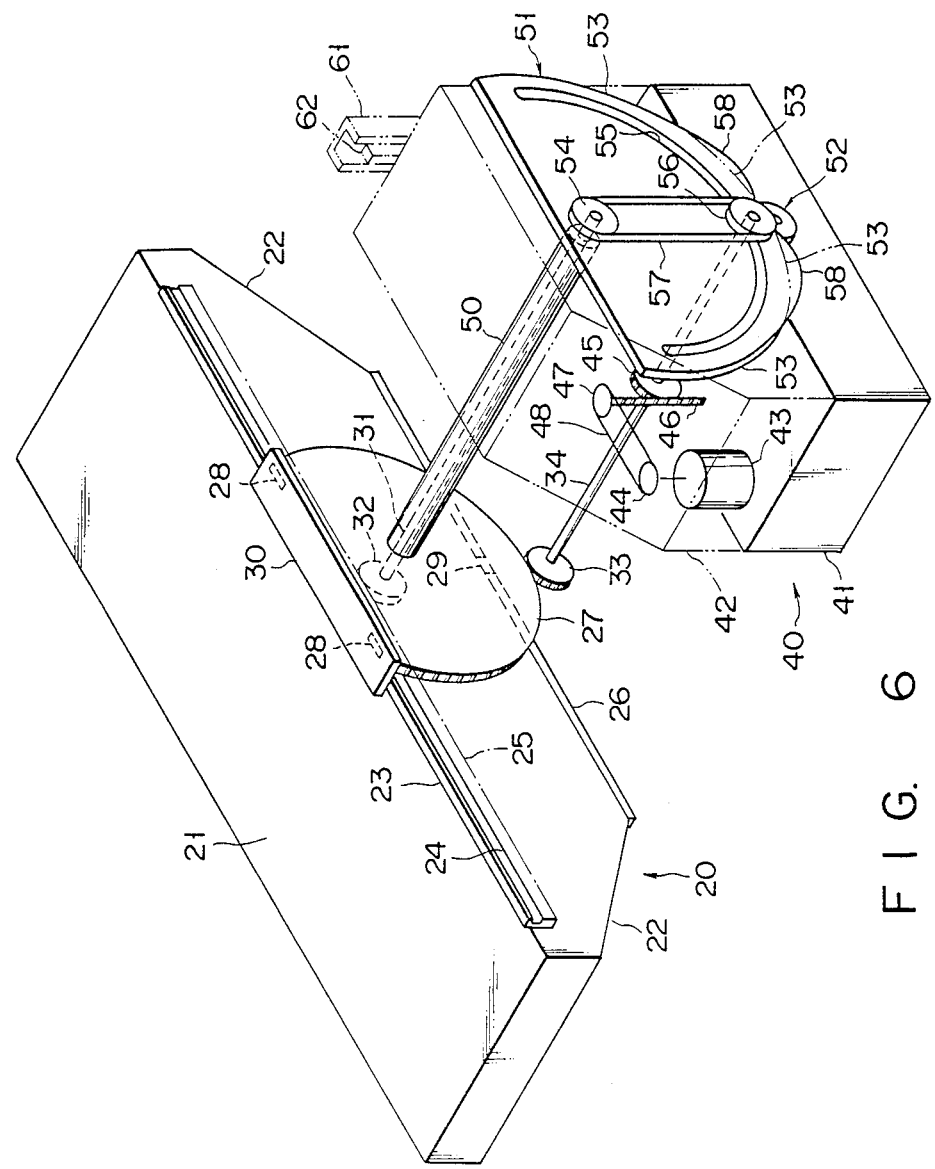
FIG. 6 is a perspective view showing a swingable and slidable bed apparatus according to the present invention.

FIG. 6 shows an example of the swingable and slidable bed apparatus according to the present invention. This bed apparatus is provided with bed 20. The top of this bed 20 is made flat and forms plane 21 on which a patient is mounted. Each of both ends 22 of bed 20 is inclined relative to patient-mounted plane 21. Guide rail 23 is attached to a side of bed 20 along the upper rim thereof. Groove 24 is formed on a side of guide rail 23 and rack 25 is formed on the bottom of guide rail 23. Another guide rail 26 is attached to the side of bed 20 along the lower rim thereof.

A semicircular gear 27 is located adjacent to the side of the bed and member 30 is attached to semicircular circular gear 27. This member 30 includes cam followers 28. Other cam follower 29 is attached to semicircular gear 27 at the lower portion thereof. Cam followers 28 are slidably fitted in groove 24 of guide rail 23. Cam follower 29 is also slidably fitted in a groove (not shown) of guide rail 26.

Shaft 31 passes through the center of semicircular gear 27 and forms the axis of rotation for semicircular gear 27, which can thus rotate round shaft 31.

Pinion 32 fixed to the foremost end of shaft 31 is engaged with rack 25 of guide rail 23. Another pinion 33 which is located under semicircular gear 27 is engaged with this semicircular gear 27. Another shaft 34 extends from pinion 33. Shafts 31 and 34 are rotated, synchronizing with each other, respectively at constant speed, as will be described later.

When shafts 31 and 34 are rotated, therefore, semicircular gear 27 is rotated by pinion 33. At the same time, rack 25 is moved by pinion 32 and cam followers 28 and 29 are slid in the grooves of the guide rails. As the result, bed 20 is swung round the axis of rotation (or shaft 31) at constant speed while being slid parallel to patient-mounted plane 21 at constant speed. Namely, semicircular gear 27, pinion 33, shaft 34, and shaft 31 (or the axis of rotation) form a means for swinging the bed. Guide rails 23, 26, cam followers 28, 29, pinion 32 and shaft 31 form a means for sliding the bed. The bed is rotated in a range of $-90°-+90°$.

Device for driving shafts 31 and 34 will be now described.

Driver device 40 includes fixed mount 41 and support 42 arranged movable up and down in relation to fixed mount 41. Shafts 31 and 34 are rotatably supported by support 42. Motor 43 is located inside the support 42. Pulley 44 is attached to the rotating shaft of motor 43 and gear 45 is attached to shaft 34. Worm 46 is engaged with gear 45. Pulley 47 is attached to the top of worm 46. Endless belt 48 is stretched between pulleys 44 and 47. When motor 43 is driven, therefore, pulley 44, belt 48, pulley 47 and worm 46 are successively rotated in this order and shaft 34 is rotated. As the result, pinion 33 is rotated.

In the case of this embodiment, bed 20 is swung and slide, and when the swinging angle of the bed is relatively small, the axis of rotation (or shaft 31) of the bed is shifted or moved upward. As the result, the bed is shifted upward. Driver device 40 is provided with a means for shifting the axis of rotation of the bed. This shift means includes cam plate 51 attached to support 42 and roller 52 attached to fixed mount 41.

Figure 1:
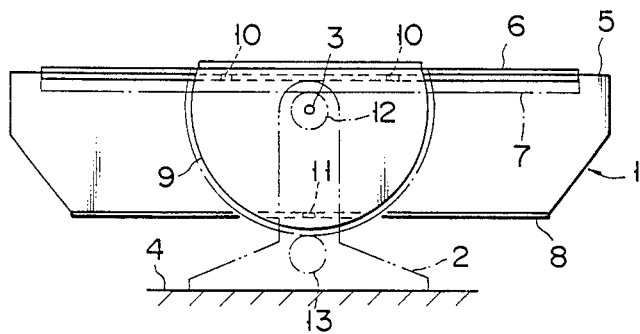
FIG. 1 is a front view showing the conventional swingable and slidable bed apparatus.
Figure 2:
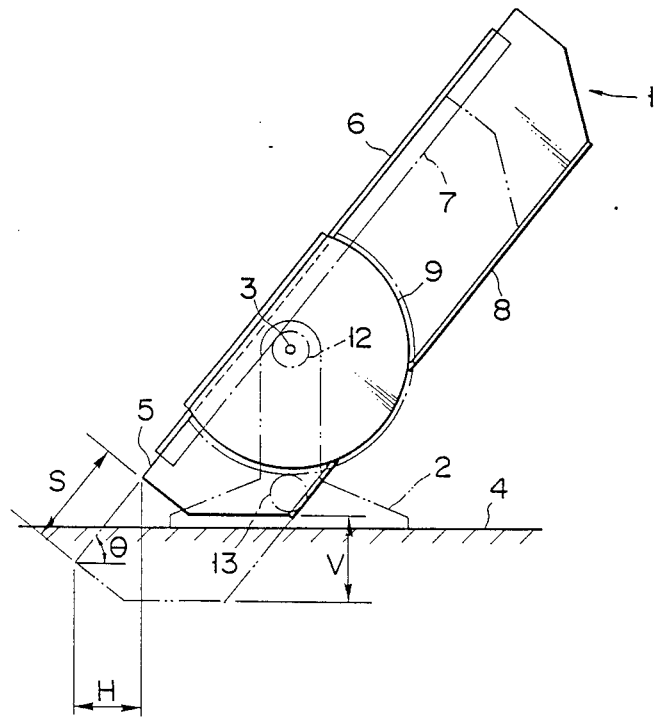
FIG. 2 is a front view showing the bed apparatus in FIG. 1 in which its bed is swung and slid.
Figure 3:
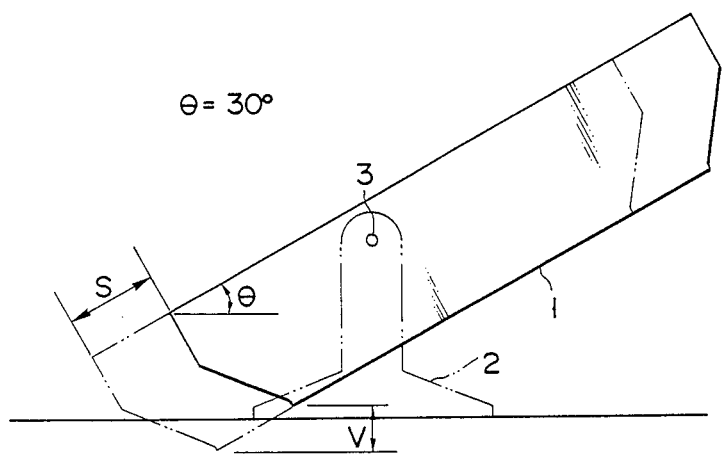
FIGS. 3 and 4 the bed swung and slid wherein the swing angle of the bed is 30° in FIG. 3 and it is 80° in FIG. 4.
Figure 4:
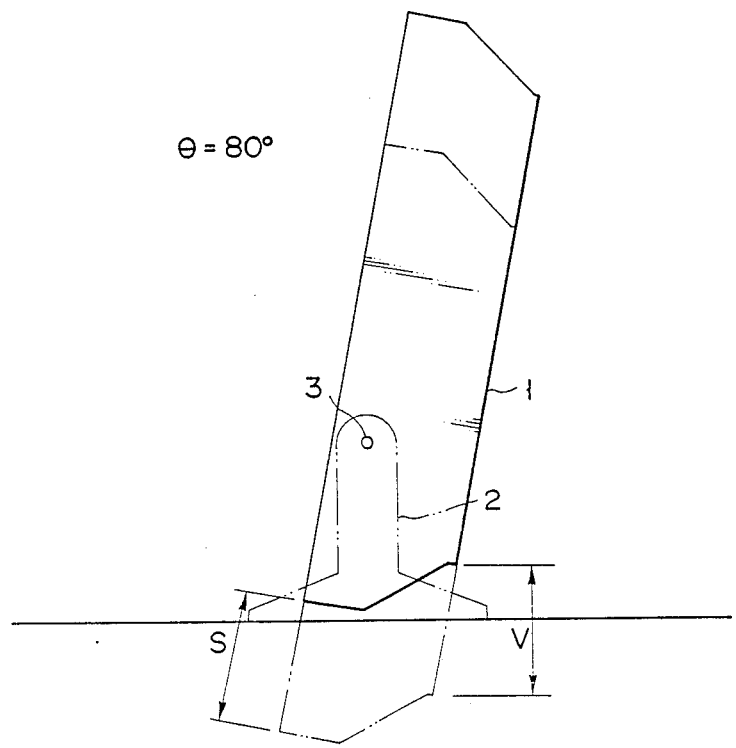
Figure 5:
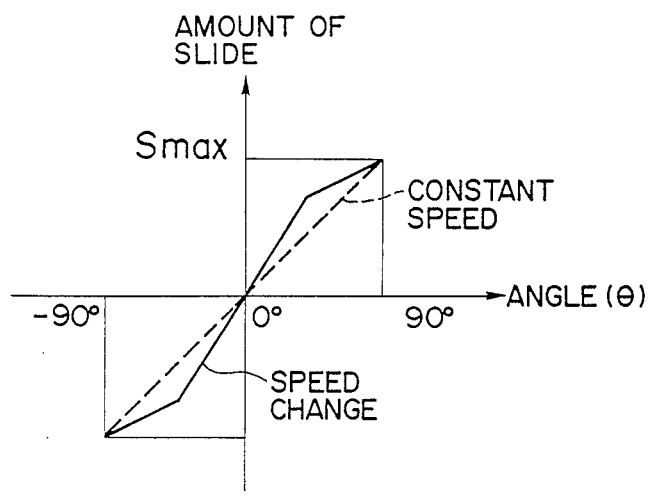
FIG. 5 is a graph showing the relation between amounts of swing and slide of the bed.
Figure 7:
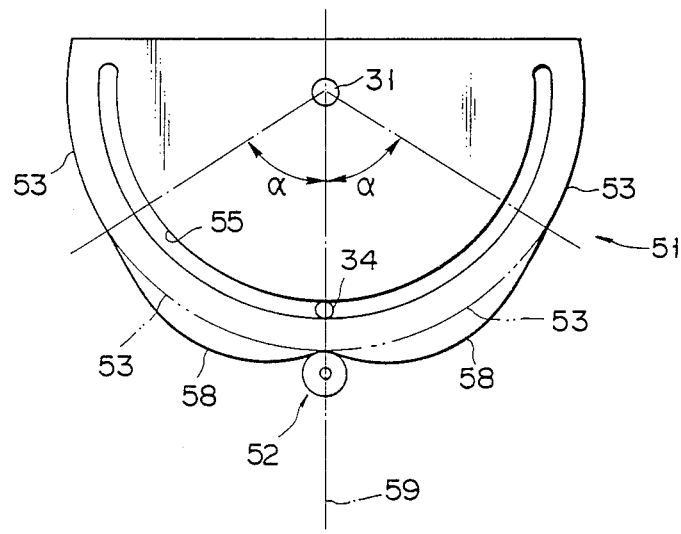
FIG. 7 is a front view showing a cam plate employed by the bed apparatus in FIG. 6.

As shown in FIGS. 6 and 7, cam plate 51 is made semicircular, having base circle 53. Cam plate 51 is rotatably supported at the center thereof by shaft 31. Cam plate 51 is therefore rotated round shaft 31. Pulley 54 is fixed to the end of shaft 31. Semicircular guide groove 55 is formed along base circle 53 of the cam plate. An end of shaft 34 is passed through this guide groove 55. Pulley 56 is attached to this end of shaft 34. Endless belt 57 is stretched between pulleys 54 and 56. When shaft 34 is rotated, pulley 56, then belt 57 and further then pulley 54 are rotated. As the result, pinion 32 is rotated and rack 25 is moved. Pinions 32 and 33 are thus driven, synchronizing with each other, respectively at constant speed by means of one motor. Further, cam plate 51 is connected to semicircular gear 27 by means of a pipe member 50. Shaft 31 is rotatably supported by pipe member 50 which is rotatably supported by support 42. Cam plate 51 is thus rotated together with semicircular gear 27.

Cam plate 51 is provided with those portions 58 which are displaced radially and outward from base circle 53. As shown in FIG. 7, the rotating angle of the cam plate is represented by that angle which is formed by vertical axis line 59 passing through the center of cam plate 51 and by a line passing between the center of cam plate 51 and any of points on the base circle. The cam plate and the semicircular gear are rotated together with each other. Therefore, the rotating angle of the cam plate is equal to the swinging angle of the bed. Each of displaced portions 58 is formed in such a range that equals to the rotating angle $\alpha$ of the cam plate. The amount of displacement of displaced portion 58 becomes zero when the rotating angle of the cam plate is 0° and $\alpha$° and it becomes maximum E when the rotating angle of the cam plate is substantially $\alpha/2$°. Cam plate 51 has first sliding faces formed on the end faces of displaced portions 58 when the rotating angle of the cam plate is smaller than $\alpha$, and it has second sliding faces formed on the end face of base circle 53 when the rotating angle of the cam plate is larger than $\alpha$. The case where the rotating angle of the cam plate is smaller than $\alpha$ corresponds to that case where the swinging angle of the bed is relatively small, and the case where the rotating angle of the cam plate is larger than $\alpha$ corresponds to that case where the swinging angle of the bed is relatively large.

Roller 52 which is rotatably supported by fixed mount 41 supports cam plate 51. When semicircular gear 27 rotates, therefore, cam plate 51 rotates together with this semicircular gear 27. When cam plate 51 rotates, the first and second sliding faces of cam plate 51 slide relative to roller 52. When the roller slides on the first sliding face of the cam plate (or the swinging angle of the bed is relatively small), cam plate 51 is thus shifted upward by the amount of displacement of displaced portion 58, as shown in FIG. 8. As the result, the axis line of rotation (or shaft 31) of the bed and then support 42 are shifted upward. The bed is thus shifted upward. When roller 52 slides on the second sliding face of the cam plate (or the swinging angle of the bed is relatively large), cam plate 51 is not shifted upward. Support 42 and the axis line of rotation (or shaft 31) of the bed are not shifted upward accordingly.

In FIG 9, a case (or first case) where the bed is only swung is shown by a two-dot and dash line, another case (or second case) where the bed is swung and slid is shown by a dot and dash line, and other case (or third case) where the bed is swung, slid and shifted is shown by a solid line. The swinging angle of the bed is 30° in FIG. 9.

One end of the bed naturally interferes with the floor in the first case. Even if the amount of slide is increased in the second case and when the swinging angle of the bed is relatively small, the amount of elevation (or vertical component in the amount of slide) is only slightly increased but the horizontal component in the amount of slide is rapidly increased. If the bed is swung and slid in the third case and when the swinging angle of the bed is relatively small. the axis line of rotation (or shaft 31) of the bed is shifted upward. As shown in FIG. 9, the axis line of rotation (or shaft 31) of the bed is shifted by $\Delta V$. The vertical component in the amount of slide can be thus further reduced by amount $\Delta V$ by which the bed is shifted upward, as compared with the first and second cases. As the result, the amount of slide can be reduced. The horizontal component in the amount of slide can be thus further reduced, as compared with the first and second cases. Therefore, the traveling distance of the bed becomes shorter in the horizontal direction and the space in which the bed is swung and slid can be made smaller accordingly.

Even if the amount of slide is increased when the swinging angle of the bed is relatively large, the horizontal component in the amount of slide is not increased so much. When the swinging angle of the bed is relatively large, therefore, it is not needed that the axis line of rotation of the bed is shifted upward to reduce the horizontal component in the amount of slide. Because the amount of elevation of the bed is increased too much, it is preferable that the axis line of rotation of the bed is not shifted upward. When the rotating angle of the cam plate is larger than $\alpha$, therefore, roller 52 slides on base circle 53 of cam plate 51 and cam plate 51 is not shifted upward accordingly.

When the amount of slide is increased in a case where the swinging angle of the bed is smaller than 45°, the horizontal component in the amount of slide is increased. Even if the amount of slide is increased in a case where the swinging angle of the bed is larger than 45°, the horizontal component in the amount of slide is not increased. It is therefore sufficient that $\alpha$ is set smaller than ±45°.

When cam plate 51 is shifted upward, the whole of support 42 in which motor 43 and the like are housed is lifted. A means for guiding this support 42 is provided for this purpose. As shown in FIG. 6, this guide means includes guide rail 61 and roller or slide member 62 sliding in a groove on the guide rail 61. Plural units of these guide rail and slide member are preferably employed.

Another means for shifting the axis line of rotation of the bed upward is intended to control a motor, detecting the amount of elevation of the bed by means of a sensor when axis line 31 is shifted upward by the motor. In this case, however, a drawback is caused that the bed is moved in step manner because the motor is feedback-controlled. The patient lying on the bed therefore feels uneasy. Further, when the sensor breaks down, there is a fear that the bed is moved in an unexpected direction. Therefore, the above-mentioned electric means is lacking of reliability.

In contrast, the present invention allows the axis line of rotation of the bed to be shifted upward when the roller slides along the cam plate. Therefore, the bed is not moved in step manner. The patient does not feel uneasy, too. There is also no fear that the bed is moved in an unexpected direction by accident because the shift means is mechanical. The bed apparatus of the present invention is therefore superior even in the viewpoint of reliability.

When the axis line of rotation (or shaft 31) of the bed is shifted upward, not only cam plate 51 but also support 42 is elevated in this embodiment. However, it is not essential to the present invention that the support is elevated. When shaft 34 includes a universal joint, for example, it is not needed that support 42 is elevated.

Figure 10:
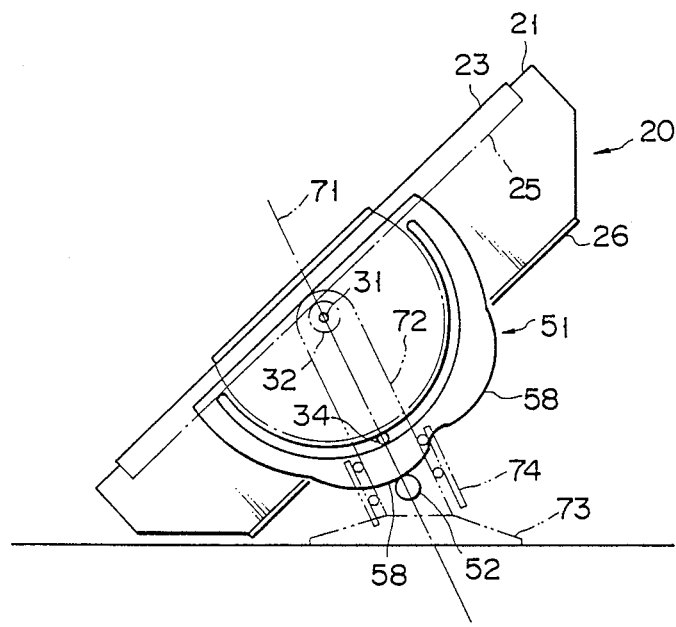
FIG. 10 is a front view showing a variation of the swingable and slidable bed apparatus according to the present invention.
Figure 11:
FIG. 11 is a vector diagram showing the direction in which the bed is shifted in the case of the bed apparatus shown in FIG. 10.

FIGS. 10 and 11 show a variation of the present invention. In the case of the above-described embodiment, the bed is swung in the range of $-90°-+90°$, taking vertical axis line 59 as its swinging center. In this variation of the present invention, however, the bed is swung in a predetermined range of $-45°-+90°$, for example, taking inclined axis line 71 as its swinging center. When the bed is swung and slid, therefore, the axis line of rotation (or shaft 31) of the bed is shifted along inclined axis line 71 in the case of this variation. Support 72 is thus extended along inclined axis line 71. This support 72 is moved in a direction inclined relative to mount 73. Members 74 for guiding support 72 are attached to mount 73.

When the bed is swung and slid in the case of this variation, cam plate 51 is shifted along inclined axis line 71 and the axis line of rotation (or shaft 31) of the bed is also shifted along inclined axis line 71. As shown in FIG. 11, therefore, this shift in the inclined direction includes vertical and horizontal components. The amount of movement of the bed in the horizontal direction can be thus directly reduced. As the result, the traveling distance of the bed in the horizontal direction can be made shorter.

What is claimed is:

1. A swingable and slidable bed apparatus supported on a floor, comprising:
   a bed having a plane on which a patient is mounted, and also having an axis line of rotation around which the bed can be swung:
   a means for swinging the bed around the axis line of rotation;
   a means for sliding the bed parallel to the patient-mounted plane while swinging the bed; and
   a means for shifting the axis line of rotation of the bed remote from the floor while swinging and sliding the bed, wherein said shift means includes a cam means rotatable around the axis line of rotation of the bed, cooperating with said swing means, and when said cam means is rotated, it is shifted in the direction remote from the floor so that the axis line of rotation of the bed can be shifted.

2. The swingable and slidable bed apparatus according to claim 1, wherein said shift means has a means for shifting the axis line of rotation of the bed in a direction vertical to the floor.

3. The swingable and slidable bed apparatus according to claim 1, wherein said shift means has a means for shifting the axis line of rotation of the bed in a direction inclined relative to the floor.

4. The swingable and slidable bed apparatus according to claim 1, further comprising a fixed mount wherein
   said cam means includes:
   a sliding member supported by the fixed mount; and
   a cam plate rotatable round the axis line of rotation of the bed, cooperating with said swing means, and sliding relative to the sliding member, and said cam plate has a base circle and portions which are displaced radially and outward from the axis line of rotation of the bed as well as from the base circle, and when the cam plate is rotated, the sliding member slides along said displaced portions of the cam plate and the cam plate is thus shifted remote from the floor so that the axis line of rotation of the bed can be shifted.

5. The swingable and slidable bed apparatus according to claim 4, wherein said shift means has a vertical axis line extending downward from the axis line of rotation of the bed and each of the displaced portions of the cam plate is formed in the range of an angle smaller than 45° when measured from the vertical axis line.

6. The swingable and slidable bed apparatus according to claim 1, wherein said swing means includes:
   a semicircular gear arranged rotatable round the axis line of rotation and slidable in relation to the bed;
   a first pinion engaged with the semicircular gear;
   a driver shaft connected to the first pinion; and
   a driver means for rotating the driver shaft.

7. The swingable and slidable bed apparatus according to claim 6, herein said slide means includes:
   a guide rail extending along the bed and provided with a rack;
   a second pinion engaged with the rack of the guide rail; and
   a rotating shaft connected to the second pinion and coaxial with the rotating axis of the bed, said rotating shaft being rotated by the driver means.

8. The swingable and slidable bed apparatus according to claim 7, further comprising a fixed mount wherein said shift means includes:
   a sliding member supported by the fixed mount; and
   a cam plate rotatable round the axis line of rotation of the bed, cooperating with the swing means, and sliding relative to the sliding member, said cam plate having a base circle and portions which are displaced radially and outward from the axis line of rotation of the bed as well as from the base circle, and when the cam plate is rotated, the sliding member slides along said displaced portions of the cam plate and the cam plate is thus shifted remote from the floor, so that the axis line of rotation of the bed can be shifted.

9. The swingable and slidable bed apparatus according to claim 8, wherein said cam plate has a guide groove, said drive shaft passes through the guide groove to project one of its ends from the guide groove, and said rotating shaft passes thought the cam plate to project one of its ends from the cam plate and supports the cam plate rotatable, and
   said drive means includes:
   a hollow member wherein said hollow member has one end fixed to the cam plate and the other end fixed to the semicircular gear, and rotatably holds the rotating shaft;
   a first pulley connected to said one end of the driver shaft which is projected from the guide groove of the cam plate;
   a second pulley connected to said one end of the rotating shaft which is projected from the cam plate; and
   a belt stretch between the first and second pulley.

10. The swingable and slidable bed apparatus according to claim 9, further comprising a support in which the driver means is housed, wherein when the cam plate is rotated and shifted remote from the floor, the rotating shaft is shifted remote from the floor and the driver shaft is also shifted remote from the floor, moving in the guide groove, so that the support can be shifted remote from the floor.

* * * * *